(12) United States Patent
Carpenter et al.

(10) Patent No.: US 10,988,728 B2
(45) Date of Patent: *Apr. 27, 2021

(54) MICROBIAL-BASED WASTE WATER TREATMENT COMPOSITIONS AND METHODS OF USE THEREOF

(71) Applicants: BiOWiSH Technologies, Inc., Cincinnati, OH (US); Cal Poly Corporation, San Luis Obispo, CA (US)

(72) Inventors: Richard Carpenter, West Chester, OH (US); Michael S. Showell, Cincinnati, OH (US); JoElla Barnes, Arcola, IL (US); Nirupam Pal, San Luis Obsipo, CA (US)

(73) Assignee: BiOWiSH Technologies, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/282,951

(22) Filed: May 20, 2014

(65) Prior Publication Data

US 2014/0342437 A1    Nov. 20, 2014

Related U.S. Application Data

(60) Provisional application No. 61/825,332, filed on May 20, 2013.

(51) Int. Cl.
| | |
|---|---|
| *C12N 1/20* | (2006.01) |
| *C12N 1/04* | (2006.01) |
| *B08B 3/04* | (2006.01) |
| *C02F 3/34* | (2006.01) |
| *C02F 103/42* | (2006.01) |
| *A23B 7/155* | (2006.01) |

(52) U.S. Cl.
CPC .............. *C12N 1/20* (2013.01); *A23B 7/155* (2013.01); *B08B 3/04* (2013.01); *C02F 3/341* (2013.01); *C02F 3/343* (2013.01); *C12N 1/04* (2013.01); *A23Y 2220/67* (2013.01); *A23Y 2280/15* (2013.01); *A23Y 2280/55* (2013.01); *C02F 2103/42* (2013.01)

(58) Field of Classification Search
None
See application file for complete search history.

(56) References Cited

U.S. PATENT DOCUMENTS

| | | | | |
|---|---|---|---|---|
| 5,627,069 | A * | 5/1997 | Powlen | A01C 3/00 210/611 |
| 6,025,152 | A | 2/2000 | Hiatt | |
| 6,410,305 | B1 * | 6/2002 | Miller | A01K 1/01 210/611 |
| 7,037,708 | B1 * | 5/2006 | Runge | C12N 1/04 424/93.4 |
| 8,747,873 | B2 | 6/2014 | Yin et al. | |
| 9,302,924 | B1 | 4/2016 | Showell et al. | |
| 9,717,767 | B2 | 8/2017 | Carpenter et al. | |
| 10,004,768 | B2 | 6/2018 | Kubo | |
| 2003/0109025 | A1 | 6/2003 | Durand et al. | |
| 2004/0042972 | A1 * | 3/2004 | Truong-Le | A61K 9/0043 424/46 |
| 2006/0188978 | A1 | 8/2006 | Grant | |
| 2007/0060477 | A1 * | 3/2007 | Pedersen | A23L 1/0345 504/100 |
| 2007/0134493 | A1 * | 6/2007 | Meghpara | A61J 3/07 428/402.2 |
| 2008/0260923 | A1 * | 10/2008 | Kratky | A23L 3/16 426/471 |
| 2009/0042267 | A1 | 2/2009 | Park | |
| 2009/0269307 | A1 | 10/2009 | Albers et al. | |
| 2011/0014278 | A1 | 1/2011 | Derrieu | |
| 2011/0110894 | A1 | 5/2011 | Drahos et al. | |
| 2011/0269220 | A1 | 11/2011 | Van Slyke | |
| 2012/0083412 | A1 * | 4/2012 | Trevino | A01N 25/26 504/117 |
| 2012/0084886 | A1 * | 4/2012 | Lopez-Cervantes | A01N 63/00 800/298 |
| 2013/0337518 | A1 | 12/2013 | Razavi-Shirazi | |
| 2014/0342437 | A1 | 11/2014 | Carpenter et al. | |
| 2015/0336828 | A1 | 11/2015 | Greenwald et al. | |
| 2016/0029666 | A1 | 2/2016 | Carpenter et al. | |
| 2016/0312252 | A1 | 10/2016 | Carpenter et al. | |

FOREIGN PATENT DOCUMENTS

| | | |
|---|---|---|
| CN | 100374547 | 3/2008 |
| CN | 101473896 A | 7/2009 |
| CN | 101503664 A | 8/2009 |

(Continued)

OTHER PUBLICATIONS

English translation of: Liu, T. et al. Yueshi lactobacillus and microbial inoculum, application and premix. Chinese Patent Application Publication No. CN 102399733A, Apr. 4, 2012. pp. 1-12. specif. p. 3.*

Encyclopedia of Food and Color Additives.Dextrose monohydrate. Soy lecithin. CRC Press (publisher).First edition.Copyright 1997. CRC Press, Inc. Ed.: George A. Burdock, Ph.D., Boca Raton, FL.pp. 797, 1553, 1554.*

Sargent, M.G. Jul. 1975. Control of cell length in Bacillus subtilis. Journal of Bacteriology 123(1): 7-19. specif. p. 10.*

British Geological Survey. Limestone. In: Mineral Planning Factsheet. Office of the Deputy Prime Minister. Copyright 2006 Crown. pp. 1-9, specif. p. 1.*

(Continued)

*Primary Examiner* — Renee Claytor
*Assistant Examiner* — Sharon M. Papciak
(74) *Attorney, Agent, or Firm* — Cooley LLP; Ivor R. Elrifi; Cynthia Kozakiewicz

(57) ABSTRACT

The present invention relates to microbial compositions useful in treating and remediating wastewater, removing organic matter from the surfaces of post harvested fruits and vegetables, and decreasing post-harvest disease in fruit and vegetables.

20 Claims, 3 Drawing Sheets

(56) References Cited

FOREIGN PATENT DOCUMENTS

| | | |
|---|---|---|
| CN | 101538538 | 9/2009 |
| CN | 102399733 A * | 4/2012 |
| CN | 102987079 A | 3/2013 |
| CN | 103 484 413 A | 1/2014 |
| CN | 104232510 | 12/2014 |
| CN | 103 087 918 B | 4/2015 |
| DE | 19617331 A1 | 11/1997 |
| EP | 0410877 A1 | 1/1991 |
| EP | 0720974 A1 | 7/1996 |
| GB | 2478929 A | 9/2011 |
| JP | 2001-299328 | 10/2001 |
| WO | WO 98/56366 A1 | 12/1998 |
| WO | 2001068808 A1 | 9/2001 |
| WO | WO 2002/078450 A1 | 10/2002 |
| WO | 2006082328 A2 | 8/2006 |
| WO | 2009038530 A1 | 3/2009 |
| WO | WO-2010138522 A2 * | 12/2010 ............... A61K 9/06 |
| WO | WO 2014/189963 A1 | 11/2014 |
| WO | WO 2015/056185 A1 | 4/2015 |
| WO | WO 2016/019017 A1 | 2/2016 |
| WO | WO 2016/070174 A1 | 5/2016 |
| WO | WO 2016/073981 A1 | 5/2016 |

OTHER PUBLICATIONS

International Search Report issued for application No. PCT/US2014/038833, dated Sep. 10, 2014.

Downes et al., "Determination of Cyanuric Acid Levels in Swimming Pool Waters by u.v. Absorbance, HPLC and Melamine Cyanurate Precipitation", Water Res., vol. 18, No. 3, pp. 277-280, (1984).

O'Brien et al., "Equilibria in Aqueous Solutions of Chlorinated Isocyanurate", In A.J. Rubin, ed. Chemistry of Water Supply, Treatment, and Distribution, Chapter 14. Ann Arbor Science Publishers, Ann Arbor, Michigan (1974).

Shields et al., "Inactivation of Cryptosporidium parvum under chlorinated recreational water conditions", Journal of Water and Health, 06.4:513-520 (2008).

Shannon, M.A.; Bohn, P.W.; Elimelech, M; Georgiadis, J.G.; Marinas, B.J.; Mayes, A.M., 2008, Science and technology for water purification in the coming decades, Nature, 452 (7185), 301-310.

Schmidt, S.P.; Basolo, F.; Trogler, W.C., 1987, Reactions between dimanganese, dirhenium, and manganese-rhenium decacarbonyl and oxidants. Inorg. Chim. Acta, 131 (2), 181-189.

Koops, H.-P.; Pommerening-Roser, A., 2001, Distribution and ecophysiology of the nitrifying bacteria emphasizing cultured species, FEMS Microbiology Ecology, 37(1), 1-9.

Hommes, N.G.; Sayavedra-Soto, L.A.; Arp, D.J., 2003, Chemolithoorganotrophic Growth of Nitrosomononas eruopaea on Fructose. Journal of Bacteriology, 185 (23), 6809-6814.

Prosser, J.I., 1989, Autotrophic nitrification in bacteria. Advances in microbial physiology, 30, 125-181.

Tramper, J; Grootjen, D.R.J., 1986, Operating performance of Nitrobacter agilis immobilized in carrageenan. Enzyme and Microbial Technology 8 (8), 477-480.

Shapleigh, J., 2006, The Denitrifying Prokaryotes. In the Prokaryotes, Dworkin, M.; Falkow, S.; Rosenberg, E.; Schleifer, K.-H.; Stackebrandt, E., Eds. Springer New York; pp. 769-792.

Verbaendert, I.; Boon, N.; De Vos, P.; Heylen, K., 2011, Denitrification is a common feature among members of the genus Bacillus. Syst Appl Microbio 34 (5), pp. 385-391.

Strous, M.; Fuerst, J.A.; Kramer, E.H.; Logemann, S.; Muyzer, G.; van de Pas-Schoonen, K.T.; Webb, R.; Kuenen, J.G.; Jetten, M.S., 1999, Missing lithotroph identified as new planctomycete. Nature 400 (6743), 446-449.

Jetten, M.S.M., Wagner, M.; Fuerst, J.; van Loosdrecht, M.; Kuenen, G.; Strous,M., 2001, Microbiology and application of the anaerobic ammonium oxidation ('anammox') process. Current Opinion in Biotechnology, 12 (3), 283-288.

Hellinga, C.; Schellen, A.A.J.C.; Mulder, J.W.; van Loosdrecht, M.C.M.; Heijnen, J.J., 1998, The Sharon process; An innovative method for nitrogen removal from ammonium-rich waste water. Water Science and Technology, 37 (9), 135-142.

Third, K.A.; Sliekers, A.O.; Kuenen, J.G.; Jetten, M.S., 2001, the CANON system (Completely Autotrophic Nitrogen-removal Over Nitrite) under ammonium limitation; Interaction and competition between three groups of bacteria. Systematic and applied microbiology 24 (4), 588-596.

Schreiber, F., 2009, Detecting and Understanding Nitric Oxide Formation during Nitrogen Cycling in Microbial Biofilms. Universitaet Bremen, Bremen, 154 pages in total.

Schmidt, I.; Sliekers, O.; Schmid, M.; Bock, E.; Fuerst, J.; Kuenen, J.G.; Jetten, M.S.M.; Strous, M., 2003, New concepts of microbial treatment processes for the nitrogen removal in wastewater. FEMS Microbiology Reviews, 481-492.

Kim, J.K.; Park, K.J.; Cho, K.S.; Nam, S.-W.; Park, T.-J.; Bajpai, R., 2005, Aerobic nitrification-denitrification by heterotrophic Bacillus strains. Bioresource Technology, 96 (17), 1897-1906.

Hageman, J.H.; Shankweiler, G.W.; Wall, P.R.; Franich, K.; McCowan, G. W.; Cauble, S.M.; Grajeda, J.; Quinones, C., 1984, Single, chemically defined sporulation medium for Bacillus subtilis; growth, sporulation, and extracellular protease production. Journal of Bacteriology, 160 (1), 438-441.

Anonymous, "Biological Help for the Human Race Wastewater Treatment Solutions," 2011, pp. 1-12, Chicago, IL, USA.

Gude et al. "Biodiesel from waste cooking oils via direct sonication", Applied Energy, vol. 109, 2013, p. 135-144.

Huang, Ting-Lin et al. "Nitrogen Removal from Micro-Polluted Reservoir Water by Indigenous Aerobic Denitrifiers", International Journal of Molecular Sciences, vol. 16, No. 4, Apr. 10, 2015, pp. 8008-8026.

Lee, Eva: "Investigation of a Commercial Product (BiOWiSH™) for Nitrogen Management", M. Sc. thesis, May 2012, pp. 1-131.

Rajakumar S. et al.: "Nitrate removal efficiency of bacterial consortium (Pseudomonas sp. KW1 and Bacillus sp. YW4) in synthetic nitrate-rich water", Journal of Hazardous Materials, vol. 157, No. 2-3, Jan. 16, 2008, pp. 553-563.

Roberts M. S. et al.: "Bacillus mojavensis sp. Nov., Distinguishable from Bacillus subtilis by Sexual Isolation, Divergence in DNA Sequence and Differences in Fatty Acid Composition", International Journal of Systematic Bacteriology, vol. 44, No. 2, Apr. 1994, pp. 256-264.

Veljkovic et al. "Biodiesel production by ultrasound-assisted transesterification: state of the art and the perspectives", Renewable and Sustainable Energy Reviews, vol. 16, 2012, p. 1193-1209.

Wang, Pan et al.: "Isolation and immobilization of new aerobic denitrifying bacteria", International Biodeterioration and Biodegradation, vol. 76, Jul. 9, 2012, pp. 12-17.

Baetge et al. "Complete nucleotide and deduced amino acid sequence of bovine phenylethanolamine N-methyltransferase: Partial amino acid homology with rat tyrosine. hydroxvlase" Proc. Natl. Acad. Sci. USA, vol. 83, p. 5454-5458, (1986).

Chan, Ada Mingwah: "Investigation of Dairy Wastewater Using Biowish TM", Master of Science Thesis, p. 1-142, (Dec. 2014).

Deng, Bin et al.: "The Denitrification Characteristics of Pseudomonas stutzeri SC221-M and Its Application to Water Quality Control in Grass Carp Aquaculture", PLOS ONE, vol. 9, No. 12, p. e114886, (Dec. 2014).

Studies on Screening and Characterization of Microorganisms with high Organic-Pollutants-Degrading Capability from Sea Cucumber (Apostichopus japonicus Selenka) Culture Ponds, Jun. 15, 2011, 12 pages.

Application Data Sheet 4950-01, "Dissolved Oxygen Measurement in Wastewater Treatment", Water and Wastewater Industry, Emerson Process Management, http://www2.emersonprocess.com/siteadmincenter/PM%20Rosemount%20Analytical%20Documents/Liq_ADS_4950-01.pdf, 4 pages (2009).

United States Environmental Protection Agency, "Final Risk Assessment of Bacillus Subtilis," Feb. 1997, 17 pages.

* cited by examiner

MICROBIAL-BASED WASTE WATER TREATMENT COMPOSITIONS AND METHODS OF USE THEREOF

RELATED APPLICATIONS

This application claims priority to and benefit of provisional application U.S. Ser. No. 61/825,332 filed on May 20, 2013, the contents of which are herein incorporated by reference in its entirety.

FIELD OF THE INVENTION

The present invention relates to wastewater treatment compositions containing microorganisms and methods of using the compositions.

BACKGROUND OF THE INVENTION

Various sewage treatment methods and plants are known. Most large municipal systems employ a series of settling ponds sequentially concentrating the solids contained in wastewater either with or without polymers for separation from liquids via mechanical separation means, such as belt presses. In order to produce a clean effluent that can be safely discharged to watercourses, wastewater treatment operations use three or four distinct stages of treatment to remove harmful contaminants.

Preliminary wastewater treatment usually involves gravity sedimentation of screened wastewater to remove settled solids. Half of the solids suspended in wastewater are removed through primary treatment. The residual material from this process is a concentrated suspension called primary sludge, which will undergo further treatment to become biosolids.

Secondary wastewater treatment is accomplished through a biological process, which removes biodegradable material. This treatment process uses microorganisms to consume dissolved and suspended organic matter, producing carbon dioxide and other by-products. The organic matter also provides nutrients needed to sustain the communities of microorganisms. As microorganisms feed, their density increases and they settle to the bottom of processing tanks, separated from the clarified water as a concentrated suspension called secondary sludge, biological sludge, waste activated sludge, or trickling filter humus.

Tertiary or advanced treatment is used when extremely high-quality effluent is required, such as direct discharge to a drinking water source. The solid residual collected through tertiary treatment consists mainly of chemicals added to clean the final effluent, which are reclaimed before discharge, and therefore not incorporated into biosolids.

What is needed are compositions and methods that can perform bioremediation, to remediate materials such as water that have an excess of unwanted biological material or other contaminating or polluting compounds.

SUMMARY OF THE INVENTION

In various aspects the invention provides compositions containing a mixture of microorganisms for degrading organic matter in augmenting the treatment of wastewater. Importantly, the compositions of the invention fully disperse in water and does not require a preactivation of the bacteria prior to use.

In various aspects the invention provides compositions for degrading organic matter. The compositions contain a mixture of *Bacillus* organisms or a mixture of *Bacillus* and *Lactobacillus*. In some embodiments the compositions contain *Bacillus subtilis*, *Bacillus amyloliquefaciens*, *Bacillus licheniformis*, *Bacillus pumilus*, *Pediococcus acidilactici*, *Pediococcus pentosaceus* and *Lactobacillus plantarum*. In other embodiments the composition contains *Bacillus subtilis*, *Bacillus amyloliquefaciens*, *Bacillus licheniformis*, *Bacillus pumilus*, *Bacillus meagerium*, *Bacillus coagulans*, and *Paenibacillus polymyxa*. Each of the organisms in the mixture is individually aerobically (*Bacillus*) or anaerobically (*Lactobacillus*) fermented, harvested, dried, and ground to produce a powder having a mean particle size of about 200 microns, with greater than about 60% of the mixture in the size range between 100-800 microns. In some embodiments, the ratio of the *Bacillus* to *Lactobacillus* is between 1:10 to 10:1. Preferably, the ratio of the *Bacillus* to *Lactobacillusis* 1:10 *Bacillus* to *Lactobacillus*. In other embodiments thethe ratio of the *Lactobacillus* is 1:1:1.

In some aspects the composition has a moisture content of less than about 5%; and a final bacterial concentration of about between $10^5$-$10^{11}$ colony forming units (CFU) per gram of the composition.

In various aspects the composition further contains an inert carrier such as dextrose monohydrate. Preferably, the dextrose monohydrate is at a concentration of about between 75-95% (w/w).

In other aspects the composition further includes an organic emulsifier. The organic emulsifier is for example, soy lecithin. Preferably, the organic emulsifier is at a concentration of about between 2 to 5% (w/w).

Also included in the invention are methods treating wastewater by contacting the wastewater with a composition containing the *Bacillus* and *Lactobacillus* mixtures of the invention. The wastewater is for example, municipal sewage, residential septic, or industrial wastewater. The wastewater contains food, fats, oils, grease, brewery, agriculture, or commodity waste. The method results in decreasing biological oxygen demand (BOD), total suspended solids (TSS) total kjeldahll nitrogen (TKN) and fats, oils and grease (FOG) in the wastewater.

Further included in the invention are methods of treating swimming pool water comprising contacting the water by contacting the wastewater with a composition containing the *Bacillus* and *Lactobacillus* mixtures of the invention. In some aspects the water is contacted by contacting a swimming pool filtration unit with the composition. In other aspects the composition is imbedded in a solid support.

In yet another aspect the invention provides methods of cleaning artificial turf, by contacting the artificial turf with a composition containing the *Bacillus* and *Lactobacillus* mixtures of the invention.

In another aspect the invention includes methods of remediating wastewater from fruit or vegetable by contacting the waste water with the *Bacillus* mixtures of the invention.

In a further aspect the invention provides methods of removing organic matter from the surfaces of fruits and vegetables by contacting the fruit or vegetable with the *Bacillus* mixtures of the invention. The method improves the shelf life and/or appearance, of the fruit or vegetables. The fruit is for example, a banana.

Also provided by the invention are methods of manufacturing the compositions of the invention. Mixtures of bacteria containing *Bacillus* and *Lactobacillus*, are manufactured by individually aerobically fermenting each *Bacillus* organism; individually anaerobically fermenting each *Lactobacillus* organism; harvesting each *Bacillus* and *Lactoba*-

*cillus* organism; drying the harvested organisms; grinding the dried organisms to produce a powder combining each of the *Bacillus* powders to produce a *Bacillus* mixture; combining each of the *Lactobacillus* powders in equal amounts to produce a *Lactobacillus* mixture and combining the *Bacillus* mixture and the *Lactobacillus* mixture at a ratio of between 1:10 to 10:1. The *Bacillus* organisms are *Bacillus subtilis, Bacillus amyloliquefaciens, Bacillus licheniformis,* and *Bacillus pumilus.* The *Lactobacillus* comprises *Pediococcus acidilactici, Pediococcus pentosaceus* and *Lactobacillus plantarum, Bacillus meagerium, Bacillus coagulans,* and *Paenibacillus polymyxa.* The mixture has a moisture content of less than about 5%; and a final bacterial concentration of between about $10^5$-$10^{11}$ colony forming units (CFU) per gram of the composition.

Mixtures of bacteria containing *Bacillus* organisms are manufactured by individually aerobically fermenting *Bacillus subtilis, Bacillus amyloliquefaciens, Bacillus licheniformis, Bacillus pumilus, Bacillus meagerium, Bacillus coagulans,* and *Paenibacillus polymyxa*; harvesting each organism, drying the harvested organisms; grinding the dried organisms to produce a powder and combining each of the *Bacillus* powders. The mixture has a moisture content of less than about 5%; and a final bacterial concentration of between about $10^5$-$10^{11}$ colony forming units (CFU) per gram of the composition.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

DETAILED DESCRIPTION OF THE INVENTION

DETAILED DESCRIPTION OF THE INVENTION

Figure 1:
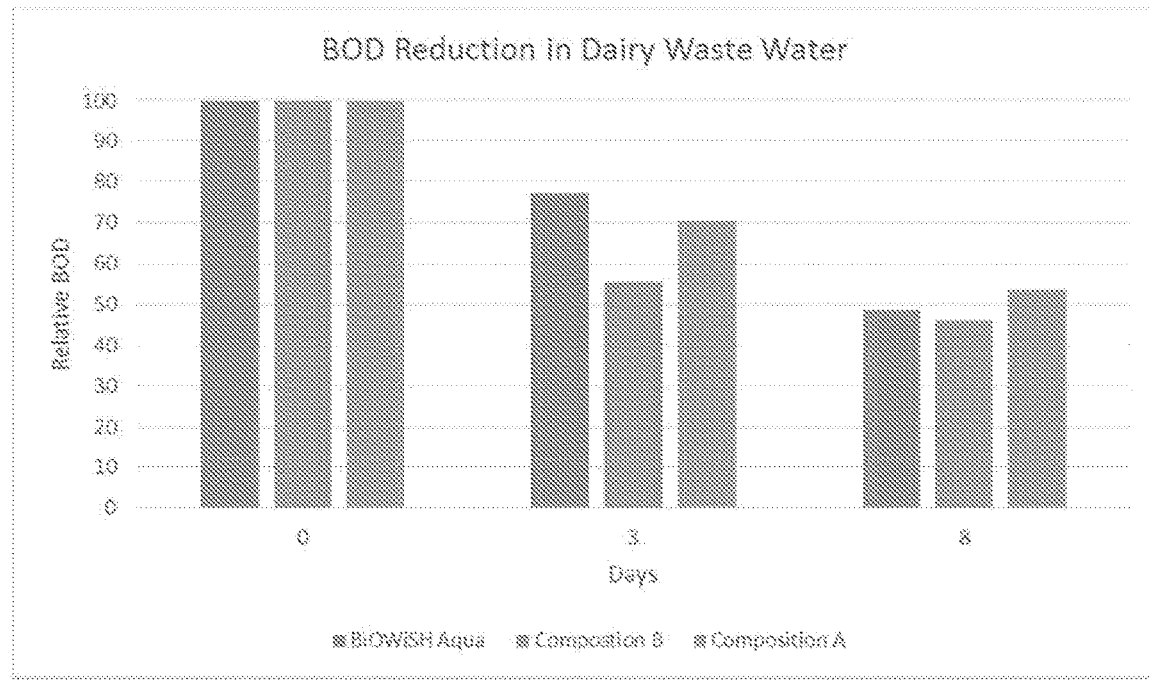
FIG. 1 shows results of BOD testing of the microbial compositions of the invention

The invention provides microbial compositions for augmenting wastewater treatment and remediation. In some aspects, the microbial compositions contain a mixture of *Bacillus* and *Lactobacillus* bacteria wherein the ratio of *bacillus* to *lactobacillus* ranges from 1:10 to 10:1. In other aspect the microbial composition contains a mixture of *Bacillus*. Specifically, the *Bacillus* and *Lactobacillus* compositions comprise mixtures of *Bacillus subtilis, Bacillus amyloliquefaciens, Bacillus licheniformis, Bacillus pumilus, Pediococcus acidilactici, Pediococcus pentosaceus* and *Lactobacillus plantarum* The *Bacillus* compositions comprise mixtures of *Bacillus subtilis, Bacillus amyloliquefaciens, Bacillus licheniformis, Bacillus pumilus, Bacillus coagulans, Bacillus megaterium,* and *Paenibacillus polymyxa.*

Importantly, the composition fully disperses upon the addition to water and unlike other wastewater treatment microbial compositions the compositions does not require a preactivation of the bacteria prior to use.

The microbial compositions reduce biological oxygen demand (BOD), total suspended solids (TSS) total kjeldahll nitrogen (TKN) and fats, oils and grease (FOG) in wastewater. The compositions are also used to degrade latexes enabling their removal from waters used to wash bananas, or other fruits and vegetables and to remove accumulating scum and algae from swimming pools. Additionally, it was surprisingly discovered that the compositions not only degrade latexes from the wastewaters resulting from the washing of bananas, or other fruits and vegetables, but also reduced the incidence of post-harvest disease in the banana harvest.

The term "microbial, bacteria" or "microbes" as used herein, refers to microorganisms that confer a benefit. The microbes according to the invention may be viable or non-viable. The non-viable microbes are metabolically-active. By "metabolically-active" is meant that they exhibit at least some residual enzyme, or secondary metabolite activity characteristic to that type of microbe.

By the term "non-viable" as used herein is meant a population of bacteria that is not capable of replicating under any known conditions. However, it is to be understood that due to normal biological variations in a population, a small percentage of the population (i.e. 5% or less) may still be viable and thus capable of replication under suitable growing conditions in a population which is otherwise defined as non-viable.

By the term "viable bacteria" as used herein is meant a population of bacteria that is capable of replicating under suitable conditions under which replication is possible. A population of bacteria that does not fulfill the definition of "non-viable" (as given above) is considered to be "viable".

"Waste holding facility" as used herein is meant a facility for the holding, storage, and treatment of organic wastes.

"Wastewater," as used herein, is principally directed to domestic sewage from dwellings, business buildings, institutions, which contain ground water, surface water, and/or storm water. Wastewater also includes water as a result of processing, or washing of products such as fruit and vegetables. For the purposes of this invention, swimming pool water is included in the definition of "wastewater".

"Treating" as used herein is means inoculating organic waste with microbes designed to enhance efficient degradation of organic matter.

Unless stated otherwise, all percentages mentioned in this document are by weight based on the total weight of the composition.

The microbes used in the product according to the present invention may be any conventional mesophilic bacteria. It is preferred that the bacteria are selected from the Lactobacillacae and Bacillaceae families. More preferably the bacteria selected form the genus *Bacillus* and *Lactobacillus* are included in the compositions of the invention.

Preferred are compositions wherein the ratio of the *Bacillus* to *Lactobacillus* is between 1:10 to 10:1. Preferably, the ratio of the *Bacillus* to *Lactobacillus* is 1:10.

Other preferred compositions are wherein the ratio of the *Lactobacillus* is preferably 1:1:1.

The levels of the bacteria to be used according the present invention will depend upon the types thereof. It is preferred that the present product contains bacteria in an amount between about $10^5$ and $10^{11}$ colony forming units per gram.

The bacteria according to the invention may be produced using any standard fermentation process known in the art. For example, solid substrate or submerged liquid fermentation. The fermented cultures can be mixed cultures or single isolates.

In some embodiments the bacteria are anaerobically fermented in the presence of carbohydrates. Suitable carbohydrates include inulin, fructo-oligosaccharide, and gluco-oligosaccharides.

The bacterial compositions are in powdered, dried form. Alternatively, the bacterial compositions are in liquid form.

After fermentation the bacteria are harvested by any known methods in the art. For example the bacteria are harvested by filtration or centrifugation.

The bacteria are dried by any method known in the art. For example the bacteria are air dried, or dried by freezing in liquid nitrogen followed by lyophilization.

The compositions according to the invention have been dried to moisture content less than 20%, 15%, 10% 9%, 8%, 7%, 6%, 5%, 4%, 3%, 2%, or 1%. Preferably, the composition according to the invention has been dried to moisture content less than 5%.

In some embodiments the dried powder is ground to decrease the particle size. The bacteria are ground by conical grinding at a temperature less than 10° C., 9° C., 8° C., 7° C., 6° C., 5° C., 4° C., 3° C., 1° C., 0° C., or less. Preferably the temperature is less than 4° C.

For example the particle size is less than 1500, 1400, 1300, 1200, 1100, 1000, 900, 800, 700, 600, 500, 400, 300, 200, or 100 microns. Preferably, the freeze dried powder is ground to decrease the particle size such that the particle size is less than 800 microns. Most preferred are particle sizes less than about 400 microns. In most preferred embodiments, the dried powder has a mean particle size of 200 microns, with 60% of the mixture in the size range between 100-800 microns. In various embodiments the freeze dried powder is homogenized.

In various embodiments the bacteria compositions are mixed with an inert carrier such as dextrose monohydrate. The dextrose monohydrate is at a concentration of at least 60%, 70%, 75%, 80%, 85%, 90%, 95% or more. Preferably, the dextrose monohydrate is at a concentration of about between 75-95% (w/w).

In other aspects the bacterial compositions contain an organic emulsifier such as, for example, soy lecithin. The organic emulsifier is at a concentration of about 1%, 2%, 3%, 4%, 5%, 5, 7%, 8%, 9% or 10%. Preferably, the organic emulsifier is at a concentration of between 2 to 5% (w/w).

Further, if desired, the bacterial compositions may be encapsulated to further increase the probability of survival; for example in a sugar matrix, fat matrix or polysaccharide matrix.

The bacterial compositions of the invention are used to treat commercial, municipal, industrial, and residential wastewater, including water in commercial, municipal and residential swimming pools. The bacterial compositions can also be used to remove organic matter from, artificial grass surfaces, such as, for example, used Astroturf.

One or more embodiments relate generally to wastewater treatment methods. A waste treatment system may receive wastewater from a community, industrial, or residential source during typical operation. For example, the wastewater may be delivered from a municipal or other large-scale sewage system. Alternatively, the wastewater may be generated, for example, by food processing or pulp and paper plants.

Wastewater may generally be any stream of waste, bearing at least one undesirable organic constituent. The waste products treatable with the present invention include, but are not limited to organic waste produced by metabolic processes, including human and animal waste, as well as industrial wastes, effluents, sewage, and the like.

The aqueous solution or the dry composition according to the invention can be employed to reduce biological oxygen demand (BOD), total suspended solids (TSS) total kjeldahll nitrogen (TKN) and fats, oils and grease (FOG) in sewage and other waste water products. The compositions of the invention may also be used to treat swimming pools to remove scum and reduce algae.

The compositions biodegrades latex from waters used to wash bananas. The compositions of the invention are also useful in removing organic material from the surfaces of fruits and vegetables, such as, for example, in the processing or washing of fruit and vegetables, e.g., which aids in improving fruit shelf life, appearance, and reducing the incidence of post-harvest disease.

Solutions of the compositions can be pumped into the material to be treated (liquid, sludge, or solid) or sprayed onto the surface, or into the airspace surrounding the material, or applied to a filter through which the water to be cleaned is passed. The dry material can be mixed into a slurry or solution at the point of application and applied in a similar manner.

The compositions or the invention are manufactured by any method suitable or productions of bacterial compositions. Preferably, mixtures of bacteria containing *Bacillus* and *Lactobacillus*, are manufactured by individually aerobically fermenting each *Bacillus* organism; individually anaerobically fermenting each *Lactobacillus* organism; harvesting each *Bacillus* and *Lactobacillus* organism; drying the harvested organisms; grinding the dried organisms to produce a powder combining each of the *Bacillus* powders to produce a *Bacillus* mixture; combining each of the *Lactobacillus* powders in equal amounts to produce a *Lactobacillus* mixture and combining the *Bacillus* mixture and the *Lactobacillus* mixture at a ratio of between 1:10 to 10:1. The *Bacillus* organisms are *Bacillus subtilis, Bacillus amyloliquefaciens, Bacillus licheniformis,* and *Bacillus pumilus*. The *Lactobacillus* comprises *Pediococcus acidilactici, Pediococcus pentosaceus* and *Lactobacillus plantarum, Bacillus meagerium, Bacillus coagulans,* and *Paenibacillus polymyxa*. The mixture has a moisture content of less than about 5%; and a final bacterial concentration of between about $10^5$-$10^{11}$ colony forming units (CFU) per gram of the composition.

Mixtures of bacteria containing *Bacillus* organisms are manufactured by individually aerobically fermenting *Bacillus subtilis, Bacillus amyloliquefaciens, Bacillus licheniformis, Bacillus pumilus, Bacillus meagerium, Bacillus coagulans,* and *Paenibacillus polymyxa;* harvesting each organism, drying the harvested organisms; grinding the dried organisms to produce a powder and combining each of the *Bacillus* powders. The mixture has a moisture content of less than about 5%; and a final bacterial concentration of between about $10^5$-$10^{11}$ colony forming units (CFU) per gram of the composition.

A better understanding of the present invention may be given with the following examples which are set forth to illustrate, but are not to be construed to limit the present invention.

EXAMPLES

Example 1

Preparation of the Microbial Species

The microbes of the present invention are grown using standard deep tank submerged fermentation processes known in the art.

*Bacillus* Species

Individual starter cultures of *Bacillus subtilis, Bacillus amyloliquefaciens, Bacillus licheniformis*, and *Bacillus pumilus* are grown according to the following general protocol: 2 grams Nutrient Broth, 2 grams AmberFerm (yeast extract) and 4 grams Maltodextrin are added to a 250 ml Erlenmeyer flask. 100 mls distilled, deionized water is added and the flask is stirred until all dry ingredients are dissolved. The flask is covered and placed for 30 min in an Autoclave operating at 121° C. and 15 psi. After cooling, the flask is inoculated with 1 ml of one of the pure microbial strains. The flask is sealed and placed on an orbital shaker at 30° C. Cultures are allowed to grow for 3-5 days. This process is repeated for each of the microbes in the mixture. In this way starter cultures of *Bacillus subtilis, Bacillus amyloliquefaciens, Bacillus licheniformis*, and *Bacillus pumilus* are prepared.

Larger cultures are prepared by adding 18 grams Nutrient Broth, 18 grams AmberFerm, and 36 grams Maltodextrin to 1 liter flasks with 900 mls distilled, deionized water. The flasks are sealed and sterilized as above. After cooling, 100 mls of the microbial media from the 250 ml Erlenmeyer flasks are added. The 1 liter flasks are sealed, placed on and orbital shaker, and allowed to grow out for another 3-5 days at 30° C.

In the final grow-out phase before introduction to the fermenter, the cultures from the 1 liter flasks are transferred under sterile conditions to sterilized 6 liter vessels and fermentation continued at 30° C. with aeration until stationary phase is achieved. The contents of each 6 liter culture flask are transferred to individual fermenters which are also charged with a sterilized growth media made from 1 part yeast extract and 2 parts dextrose. The individual fermenters are run under aerobic conditions at pH 7.0 and the temperature optimum for each species:

| Microbe | Temperature Optimum |
| --- | --- |
| *Bacillus subtilis* | 35° C. |
| *Bacillus amyloliquefaciens* | 30° C. |
| *Bacillus licheniformis* | 37° C. |
| *Bacillus pumilus* | 32° C. |

Each fermenter is run until cell density reaches $10^{11}$ CFU/ml, on average. The individual fermenters are then emptied, filtered, and centrifuged to obtain the bacterial cell mass which is subsequently dried under vacuum until moisture levels drop below 5%. The final microbial count of the dried samples is $10^{10}$-$10^{11}$ CFU/g.

*Lactobacillus* Species

Individual, purified isolates of *Pediococcus acidilactici, Pediococcus pentosaceus* and *Lactobacillus plantarum* are grown-up in separate fermenters using standard anaerobic submerged liquid fermentation protocols at the pH and temperature optimum for each species:

| Microbe | pH Optimum | Temperature Optimum |
| --- | --- | --- |
| *Pediococcus acidilactici* | 5.5 | 37° C. |
| *Pediococcus pentosaceus* | 5.5 | 37° C. |
| *Lactobacillus plantarum* | 6.0 | 35° C. |

After fermentation the individual cultures are filtered, centrifuged, freeze dried to a moisture level less than about 5%, then ground to a particle size of about 200 microns.

The dried *bacillus* and *lactobacillus* microbes are combined to give a final dried microbial composition comprising *Bacillus subtilis, Bacillus amyloliquefaciens, Bacillus licheniforms, Bacillus pumilus, Pediococcus acidilactici, Pediococcus pentosaceus*, and *Lactobacillus plantarum*, at a ratio of total *bacillus* to *lactobacillus* between 1:10 and 10:1 with a microbial activity between $10^8$ and $10^{10}$ CFU/g.

Example 2

Preparation of the Microbial Species Via Solid Substrate Fermentation

The microbial mix of the present invention can also be prepared via solid substrate fermentation according to the following process:

*Bacillus* Species

Four pounds of Dairy 12% Mineral Mix, 60 lbs Rice bran, and 30 lbs Soybean meal were added to a jacketed, horizontal mixer with screw auger. Water and steam were added with mixing to obtain slurry. After mixing for 2 minutes, 300 lbs wheat bran was added to the mixer followed by more water and steam to re-make the slurry. With the mixer temperature controlled to 35-36° C., 4 lbs of a dry microbial mixture comprising *Bacillus subtilis, Bacillus amyloliquefaciens, Bacillus licheniformis* and *Bacillus pumilus* with an initial microbial activity of about $1 \times 10^{10}$ CFU/g, were added. The mixer was closed; temperature adjusted to 34° C., and the contents allowed to mix for up to 4 days. After fermentation the contents of the mixer were emptied onto metal trays and allowed to air dry. After drying, a product was ground to a particle size below about 200 microns. The final *bacillus* product obtained had a microbial count on the order of $1 \times 10^{11}$ CFU/g and less than about 5% moisture.

*Lactobacillus* Species

A mixed culture of *Pediococcus acidilactici, Pediococcus pentosaceus* and *Lactobacillus plantarum* was fermented under GMP conditions for up to 5 days on a mixture comprised of: 1 part inulin, 2.2 parts isolated soy protein, 8 parts rice flour with 0.25% w/w sodium chloride, 0.045% w/w Calcium carbonate, 0.025% w/w Magnesium sulphate, 0.025% w/w Sodium phosphate, 0.012% w/w Ferrous sulphate and 29.6% water. Upon completion of fermentation the mixture was freeze dried to a moisture content less than 5%, ground to a particle size below 800 microns and homogenized. The final microbial concentration of the powdered product is between $10^9$ and $10^{11}$ CFU/g.

Final Microbial Mix

The dried *bacillus* and *lactobacillus* microbes were combined in ratios between 1:10 and 10:1 to give a final dried microbial composition comprising *Bacillus subtilis, Bacillus amyloliquefaciens, Bacillus licheniformis, Pediococcus acidilactici, Pediococcus pentosaceus*, and *Lactobacillus plantarum* with a microbial activity between $10^8$ and $10^{10}$ CFU/g.

Example 3

Identification of Optimum *Bacillus* and *Lactobacillus* Ratios for BOD Reduction Two microbial compositions were prepared by mixing the individual dried microbes (*bacillus* and *lactobacillus*) from Example 1 in a ratio of 1:1 (Composition A) and 1:10 (Composition B). These two compositions were compared for their ability to reduce BOD of dairy lagoon wastewater (FIG. 1). A commercial wastewater product (BiOWiSH Aqua, made in Thailand) was included as a positive control These results show that the 1:10 ratio of *Bacillus* to *Lactobacillus* (Composition B) is preferred for rapid reduction of BOD.

Example 4

Formulation of the Wastewater Product using Microbes from Example 1

The individual dried microbes (*bacillus* and *lactobacillus*) from Example 1 were mixed together in the ratio 1:10 (*Bacillus:Lactobacillus*). This dried microbial mix was diluted 1:100 with dextrose (Clintose® Industrial Dextrose). To this mix was added 3% by weight of powdered soy lecithin (Nealanders International, Inc.). The final microbial count of this composition was $1 \times 10^8$ CFU/g.

Example 5

Formulation of Wastewater Product using Process From Example 2

The *bacillus* and *lactobacillus* solid substrate fermentation products from Example 2 were ground to about 200 micron average particle size, mixed together in equal proportion then mixed with 3% by weight powdered soy lecithin (Nealanders International, Inc). A final product was obtained with a microbial count of $10^8$-$10^9$ CFU/g and moisture below 5%.

Example 6

Performance of the Waste Water Product from Example 4 in Septic Treatment

Figure 2:
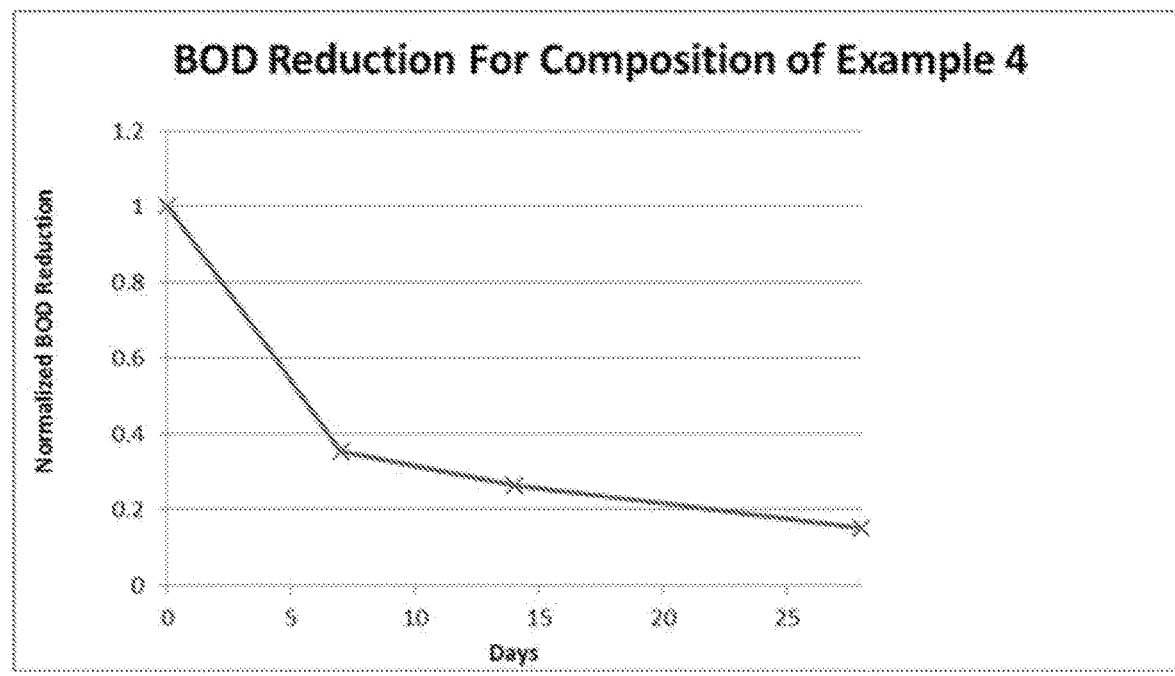
FIG. 2: shows results of BOD Reduction in Residential LPP Systems
Figure 3:
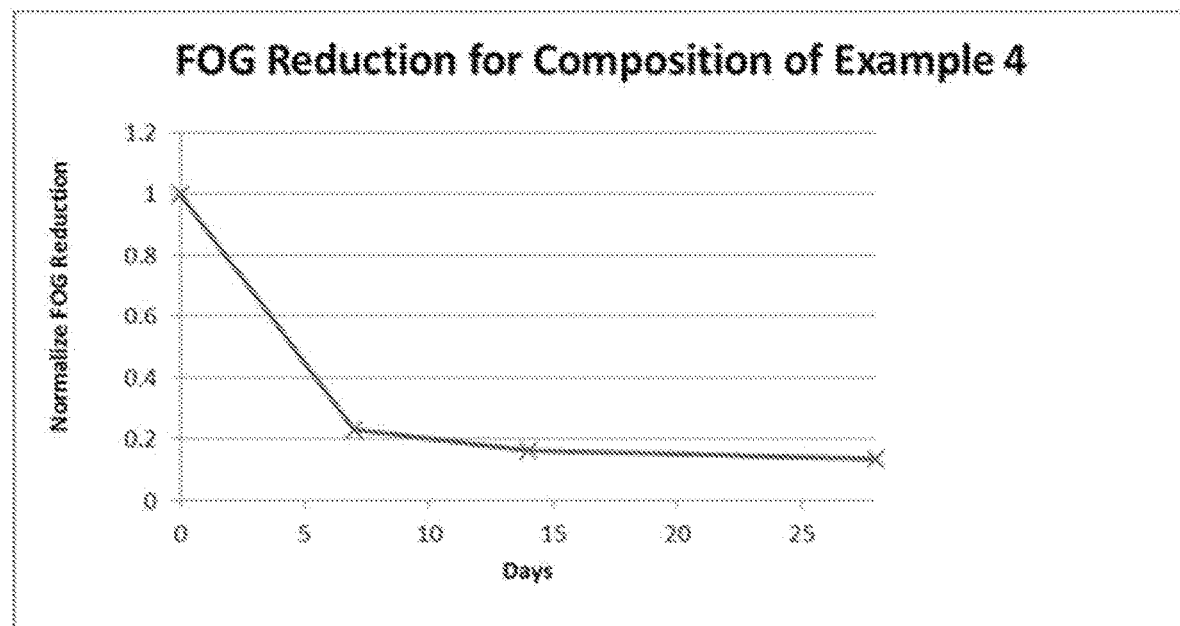
FIG. 3: shows the FOG Reduction in Residential LPP Systems
Figure 4:
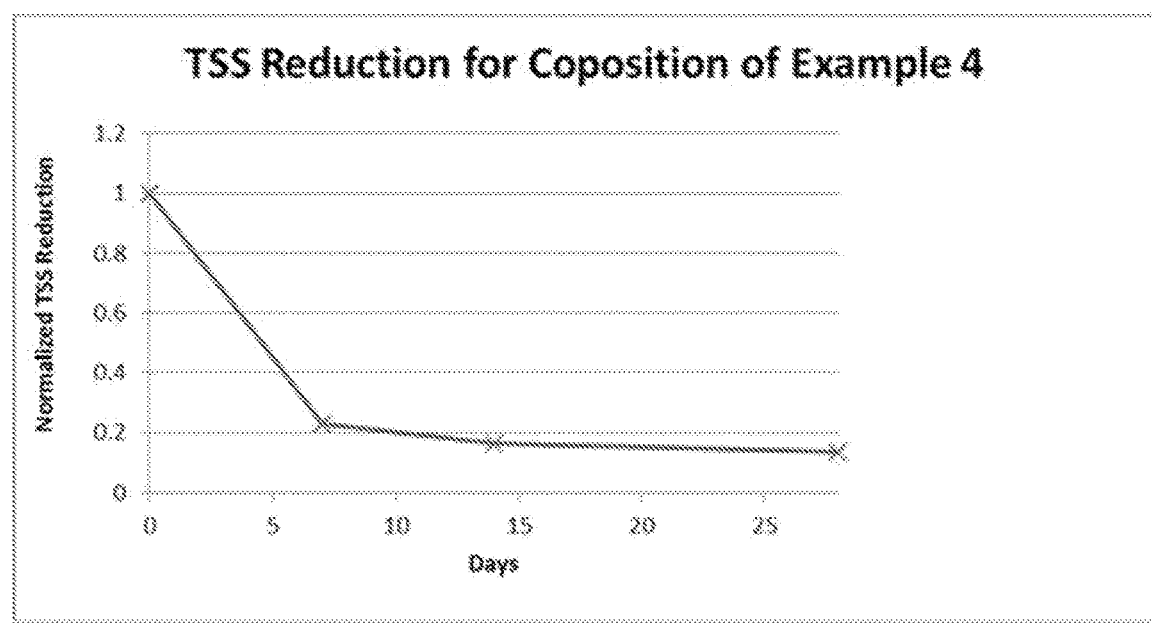
FIG. 4: shows the TSS Reduction in Residential LPP Systems

Three residential Low Pressure Pipe (LPP) septic systems located in central North Carolina, USA, were selected for testing. Baseline determinations of BOD (Biological Oxygen Demand), TSS (Total Suspended Solids), and FOG (Fats Oil and Grease) were made then 200 g of the Wastewater Treatment formulation from Example 4 were added to each system every week for a period up to 8 weeks. Weekly recordings of BOD, TSS, and FOG were made for each system. Results, averaged across the 3 LPP septic systems, showed significant reduction in the key biochemical measures versus baseline for all three systems (FIGS. 2-4).

Example 7

Performance of the Waste Water Product from Example 5 in Septic Treatment

Three residential LPP septic systems in central North Carolina, USA, were selected for this study. A baseline determination of BOD, TSS, TKN, and FOG was made for each system then 200 grams of the composition from Example 5 were added to each system every week for a period up to 8 weeks. BOD, TSS, TKN, and FOG were recorded weekly for each of the three systems. Results, averaged across the 3 LPP septic systems, show significant reduction in the key biochemical measures versus baseline for all three systems:

| | BOD (mg/l) | | | | | | |
|---|---|---|---|---|---|---|---|
| | Treatment | Baseline | Day 7 | Day 14 | Day 28 | Day 56 | % Reduction vs. Baseline |
| System | US EPA Regulation level | 350 | 350 | 350 | 350 | 350 | |
| LPP Avg. | 200 g weekly dosage of the wastewater composition from Example 5 | 1636 | 564 | 293 | 236 | 189 | 88.5 |

| | TSS (mg/l) | | | | | | |
|---|---|---|---|---|---|---|---|
| | Treatment | Baseline | Day 7 | Day 14 | Day 28 | Day 56 | % Reduction vs. Baseline |
| System | US EPA Regulation Level | 100 | 100 | 100 | 100 | 100 | |
| LPP Avg. | 200 g weekly dosage of the wastewater composition from Example 5 | 622.6 | 345.8 | 196 | 63.4 | 58.7 | 90.6 |

| | | | TKN (mg/l) | | | | |
|---|---|---|---|---|---|---|---|
| | Treatment | Baseline | Day 7 | Day 14 | Day 28 | Day 56 | % Reduction vs. Baseline |
| System | US EPA Regulation Level | 100 | 100 | 100 | 100 | 100 | |
| LPP Avg. | 200 g weekly dosage of the wastewater composition from Example 5 | 103.8 | 50.3 | 62.7 | 42.8 | 57.8 | 44.4 |

| | | | FOG (mg/l) | | | | |
|---|---|---|---|---|---|---|---|
| | Treatment | Baseline | Day 7 | Day 14 | Day 28 | Day 56 | % Reduction vs. Baseline |
| System | US EPA Regulation Level | 30 | 30 | 30 | 30 | | |
| LPP Avg. | 200 g weekly dosage of the wastewater composition from Example 5 | 280.3 | 104.7 | 46.7 | 34.2 | 111 | 60.4 |

Example 8

Reduction in BOD Compared to Competitive Product

Waste water was collected from local dairy lagoons in California's Central Valley area. Samples were pooled to create a common stock solution. The stock waste water was pipetted into several 300 ml BOD bottles and the following experimental design set-up:

| Bottle | Treatment |
|---|---|
| 1 | Control A (no added microbes) |
| 2 | Control B (no added microbes) |
| 3-10 | 100 ppm of the waste water treatment from Example 4. |
| 11-13 | 100 ppm of a commercial, mixed microbe waste water treatment product (BiOWiSH ™ Aqua FOG) |

Initial BOD was measured for each Bottle then again after storage at 30° C. for 5 days. On average, the control showed a BOD reduction of 669 mg/l versus 742 mg/l for the wastewater treatment composition from Example 4 and 701 mg/l for the commercial product.

| Bottle | $BOD_5$ Initial (mg/l) | $BOD_5$ Final (mg/l) | Avg. BOD reduction (mg/l) | Avg. BOD reduction vs. Control (mg/l) |
|---|---|---|---|---|
| 1 | 825 | 117 | 669 | — |
| 2 | 813 | 183 | | |
| 3 | 900 | 128 | 742 | 10.9% |
| 4 | 926 | 238 | | |
| 5 | 914 | 120 | | |
| 6 | 836 | 89 | | |
| 7 | 886 | 102 | | |
| 8 | 870 | 131 | | |
| 9 | 930 | 302 | | |
| 10 | 887 | 102 | | |
| 11 | 842 | 118 | 701 | 4.8% |
| 12 | 812 | 139 | | |
| 13 | 879 | 174 | | |

Example 9

Reduction in Total Suspended Solids Versus Competitive Product

Waste water was collected from the dairy lagoon pond at California Polytechnic State University in San Luis Obispo, Calif., distributed among several 2 liter bottles and the following experimental design set-up:

| Bottle | Treatment |
|---|---|
| 1 | Control (no added microbes) |
| 2-4 | 100 ppm of the waste water treatment from Example 5. |
| 5 | 100 ppm of a commercial, mixed microbe waste water treatment product (BiOWiSH ™ Aqua FOG) |

The bottles were kept at 30° C. for 5 weeks. Every week, two 50 ml aliquots were collected and dried at 90° C. for Total Solids determination:

| | TSS (mg/l) | | | | | | |
|---|---|---|---|---|---|---|---|
| Week | 0 | 1 | 2 | 3 | 4 | 5 | % Final TSS Reduction |
| Bottle 1 (Control) Average | 1819.7 | 1026.7 | 933.3 | 600.0 | 453.3 | 386.7 | 78.8 |
| Bottle 2 Average | 1750.0 | 866.7 | 626.7 | 413.3 | 453.3 | 200.0 | 88.6 |
| Bottle 3 Average | 1916.7 | 1080.0 | 720.0 | 640.0 | 480.0 | 80.0 | 95.8 |
| Bottle 4 Average | 2125.0 | 1173.3 | 786.7 | 546.7 | 133.3 | 93.3 | 95.6 |
| Bottle 5 Average | 1708.3 | 1120.0 | 813.3 | 666.7 | 333.3 | 346.7 | 79.7 |

The bottles containing the wastewater treatment from Example 5 showed higher overall percent TSS reduction than both the control and the commercial product.

Example 10

Comparison Versus Competitive Septic Treatment System

Several residential LPP septic systems in central North Carolina, USA, were selected for this study. A baseline determination of BOD, TSS, TKN, and FOG was made for each system then each system was treated weekly either with 200 grams of the composition from Example 5 or 200 gram of a commercial product (BiOWiSH™ Aqua FOG). BOD, TSS, TKN, and FOG were recorded weekly for each system. Results, averaged across the LPP septic systems, are shown below:

(BOD (mg/l))

| | Treatment | Baseline | Day 7 | Day 14 | Day 28 | Day 56 | % Reduction vs. Baseline |
|---|---|---|---|---|---|---|---|
| System | US EPA Regulation level | 350 | 350 | 350 | 350 | 350 | |
| Avg. of LPP systems treated with Example 5 Composition | 200 g weekly dosage of the wastewater composition from Example 5 | 1636 | 564 | 293 | 236 | 189 | 88.5 |
| Avg. of LPP systems treated with Commercial Product | 200 g weekly dosage of commercial septic treatment products | 2020 | 502 | 760 | 382 | 518 | 74.4 |

TSS (mg/l)

| | Treatment | Baseline | Day 7 | Day 14 | Day 28 | Day 56 | % Reduction vs. Baseline |
|---|---|---|---|---|---|---|---|
| System | US EPA Regulation Level | 100 | 100 | 100 | 100 | 100 | |
| Avg. of LPP systems treated with Example 5 Composition | 200 g weekly dosage of the wastewater composition from Example 5 | 622.6 | 345.8 | 196 | 63.4 | 58.7 | 90.6 |
| Avg. of LPP systems treated with Commercial Product | 200 g weekly dosage of commercial septic treatment products | 720 | 2540 | 413 | 652 | 123 | 98.3 |

TKN (mg/l)

| | Treatment | Baseline | Day 7 | Day 14 | Day 28 | Day 56 | % Reduction vs. Baseline |
|---|---|---|---|---|---|---|---|
| System | US EPA Regulation Level | 100 | 100 | 100 | 100 | 100 | |
| Avg. of LPP systems treated with Example 5 Composition | 200 g weekly dosage of the wastewater composition from Example 5 | 103.8 | 50.3 | 62.7 | 42.8 | 57.8 | 44.4 |
| Avg. of LPP systems treated with Commercial Product | 200 g weekly dosage of commercial septic treatment products | 98 | 91 | 51 | 96 | 53 | 45.9 |

FOG (mg/l)

| | Treatment | Baseline | Day 7 | Day 14 | Day 28 | Day 56 | % Reduction vs. Baseline |
|---|---|---|---|---|---|---|---|
| System | US EPA Regulation Level | 30 | 30 | 30 | 30 | 30 | |

-continued

| | | | | FOG (mg/l) | | | |
|---|---|---|---|---|---|---|---|
| Treatment | | Baseline | Day 7 | Day 14 | Day 28 | Day 56 | % Reduction vs. Baseline |
| Avg. of LPP systems treated with Example 5 Composition | 200 g weekly dosage of the wastewater composition from Example 5 | 280.3 | 104.7 | 46.7 | 34.2 | 111 | 60.4 |
| Avg. of LPP systems treated with Commercial Product | 200 g weekly dosage of commercial septic treatment products | 113 | 160 | 251 | 49 | 69 | 38.9 |

Example 11

Remediation of Waste Water from Fruit Washing

The composition of Example 4 was used to treat the waste water from banana washing. Latex fluid is released when bananas are harvested. Typically, the bananas are immersed in moving water to remove the latex. The waste water that results from this process is generally high in latex concentration limiting the ability to recycle and reuse.

A test program was set-up in collaboration with Coorporación Bananera Nacional (Costa Rica) to evaluate the ability of the waste water treatment compositions of the present invention to remove latex and reduce incidence of post-harvest disease.

Samples were collected from waste water pools formed from washing piles of bananas. The samples were collected late in the day when organic load in the water was highest.

Figure 5:
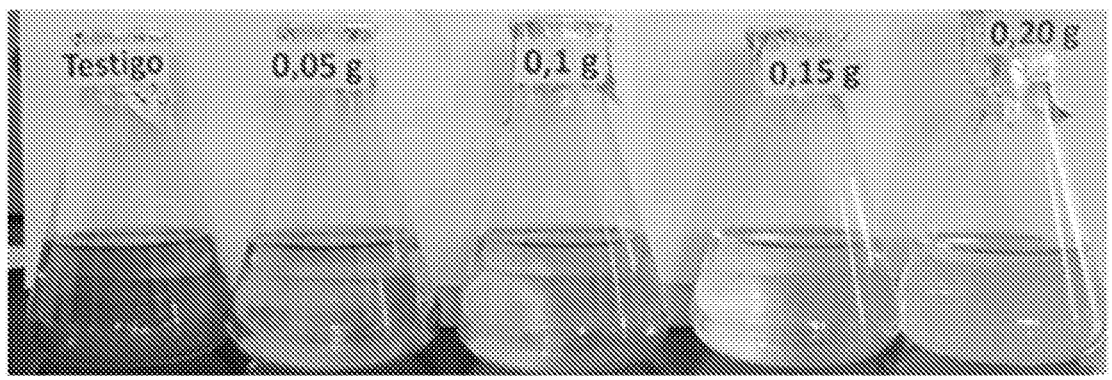
FIG. 5 is a photograph showing the reduction of turbidity of banana wash water upon treatment with the compositions of the invention.

Between 150 and 200 mls of waste water were placed in 250 ml Erlenmeyer flasks to which various concentrations of the waste water treatment composition from Example 4 were added. The flasks were incubated for 12-72 hours at 24-26° C. with mild agitation (50 rpm on an orbital shaker). The microbial composition of the present invention was found to significantly reduce turbidity of the solutions after 72 hours. (FIG. 5)

Based on these results a larger field trial was executed. On Day's 1 and 2 of the field trial, banana wash water was treated with the dispersant Bactrol® 500. 6.5 liters of Bactrol® were diluted into 60 liters of water and applied to bananas on the day of harvest via a drip system placed one meter above the banana stack. Chlorine was injected into the water stream at a level of 2-3 mg/l throughout the day. On days 3 and 4 of the test, the water was treated only with the waste water treatment composition of Example 4 plus citric acid

| | | Conventional Treatment | |
|---|---|---|---|
| DAY | Bactrol ® 500 | Chlorine | Comments |
| 1 | 6.5 Liters in 60 liters of water applied to the bananas during the day via drip | Injected into the input pipe during the day to maintain a concentration between 2-3 mg/l | Water was not changed at the end of the day and was used again the next day |
| 2 | 6.5 Liters in 60 liters of water applied to the bananas during the day via drip | Injected into the input pipe during the day to maintain a concentration between 2-3 mg/l | Water was discarded at the end of day two. |

| | | | Bioremediation Treatment | | |
|---|---|---|---|---|---|
| DAY | Cleaning Pool (101m3) | Drip Tank (50 liters) | Injection Tank (50 Liters) | Citric Acid in Cleaning pool | Comments |
| 3 | 101 g of the composition from Example 4 | | | | All pools filled with clean water to begin the next phase of the trial |
| 4 | | 150 g of the composition from Example 4 (6:00 am) | 150 g of the composition from Example 4 (6:00 am) + 50 g (1:00 pm) | 1 kg (7 am) 1 kg (10 am) 1 kg (1 pm) | |

-continued

| DAY | Cleaning Pool (101m3) | Drip Tank (50 liters) | Injection Tank (50 Liters) | Citric Acid in Cleaning pool | Comments |
|---|---|---|---|---|---|
| | | | Bioremediation Treatment | | |
| 5 | | 150 g of the composition from Example 4 (6:00 am) | 150 g of the composition from Example 4 (6:00 am) + 50 g (1:00 pm) | 1 kg (7 am) 1 kg (10 am) 1 kg (1 pm) | |

Figure 6:
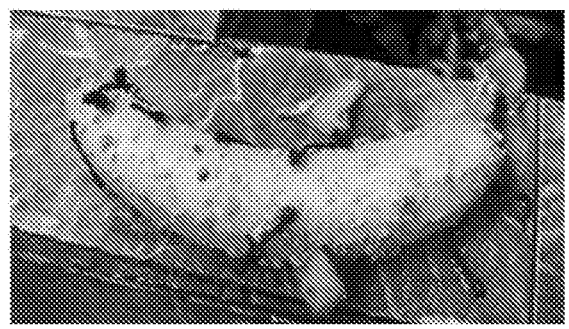
FIG. 6 are photographs showing bananas treated conventionally (A) and with the compositions of the invention (B) is a photograph showing the reducing of turbidity of banana wash water upon treatment with the compositions of the invention.
Figure 6:
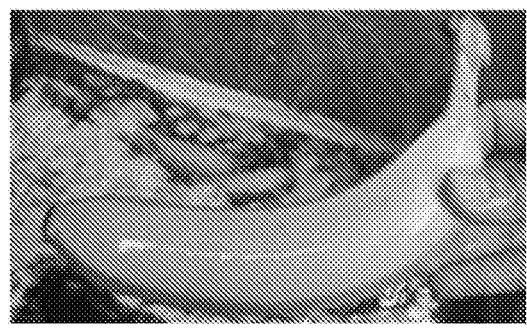

FIG. 6 compares bananas washed with the conventional treatment versus those washed with the composition from Example 4.

Example 12

Swimming Pool Treatment

The microbial composition from Example 5 is dissolved in water at a concentration of 100 g dried microbial product/liter. With the pump off, the microbial solution is poured into the filter unit of a residential swimming pool having a noticeable scum layer on the surface and allowed to stand for 1 hour before the pump is turned-on. Within 24 hours the scum is significantly reduced and in 48 hours there is no visible scum remaining.

Example 13

Expanded Microbial Composition for Wastewater Treatment and Fruit/Vegetable Wash A composition comprising the bacterial strains from Example 1 and additional microbes selected for their ability to provide additional waste water treatment and fruit/vegetable wash benefits was designed using a fermentation system similar to that developed in Example 1:

*Bacillus* and *Paenibacillus* species

Individual starter cultures of *Bacillus subtilis, Bacillus amyloliquefaciens, Bacillus licheniformis, Bacillus Pumilus, Bacillus coagulans, Bacillus megaterium*, and *Paenibacillus polymyxa*, were grown according to the following general protocol: 2 grams Nutrient Broth, 2 grams AmberFerm (yeast extract) and 4 grams Maltodextrin were added to a 250 ml Erlenmeyer flask. 100 milliters distilled, deionized water were added and the flask was stirred until all dry ingredients were dissolved. The flask was covered and placed for 30 min in an Autoclave operating at 121° C. and 15 psi. After cooling, the flask was inoculated with 1 ml of one of the pure microbial strains. The flask was sealed and placed on an orbital shaker at 30° C. Cultures were allowed to grow for 3-5 days. This process was repeated for each of the microorganism in the mixture. In this way starter cultures of *Bacillus subtilis, Bacillus amyloliquefaciens, Bacillus licheniformis, Bacillus Pumilus, Bacillus coagulans, Bacillus megaterium*, and *Paenibacillus polymyxa* were prepared.

Larger cultures were prepared by adding 18 grams Nutrient Broth, 18 grams AmberFerm, and 36 grams Maltodextrin to 1 liter flasks with 900 mis distilled, deionized water. The flasks were sealed and sterilized as above. After cooling, 100 mis of the microbial media from the 250 ml Erlenmeyer flasks were added. The 1 liter flasks were sealed, placed on and orbital shaker, and allowed to grow out for another 3-5 days at 30° C.

In the final grow-out phase before introduction to the fermenter, the cultures from the 1 liter flasks were transferred under sterile conditions to sterilized 6 liter vessels and fermentation continued at 30° C. with aeration until stationary phase was reached. The contents of each 6 liter culture flask was transferred to individual fermenters which were also charged with a sterilized growth media made from 1 part yeast extract and 2 parts dextrose. The individual fermenters were run under aerobic conditions at pH 7 at the temperature optimum for each species:

| Microbe | Temperature Optimum |
|---|---|
| *Bacillus subtilis* | 35° C. |
| *Bacillus amyloliquefaciens* | 30° C. |
| *Bacillus licheniformis* | 37° C. |
| *Bacillus coagulans* | 37° C. |
| *Bacillus megaterium* | 30° C. |
| *Bacillus pumilus* | 32° C. |
| *Paenibacillus polymyxa* | 30° C. |

Each fermenter was run until cell density reached $10^{11}$ CFU/ml, on average. The individual fermenters were then emptied, filtered, and centrifuged to obtain the bacterial cell mass which was subsequently dried under vacuum until moisture levels drop below 5%. The final microbial count of the dried samples was $10^{10}$-$10^{11}$ CFU/g.

*Lactobacillus* Species

Individual, purified isolates of *Pediococcus acidilactici, Pediococcus pentosaceus* and *Lactobacillus plantarum* were grown-up in separate fermenters using standard anaerobic submerged liquid fermentation protocols at the pH and temperature optimum for each species:

| Microbe | pH Optimum | Temperature Optimum |
|---|---|---|
| *Pediococcus acidilactici* | 5.5 | 37° C. |
| *Pediococcus pentosaceus* | 5.5 | 37° C. |
| *Lactobacillus plantarum* | 6.0 | 35° C. |

After fermentation the individual cultures were filtered, centrifuged, freeze dried to a moisture level less than about 5%, then ground to a particle size of about 100 microns The dried *bacillus* and *lactobacillus* microbes were combined in equal proportion to give a final dried microbial composition comprising *Bacillus subtilis, Bacillus amyloliq-* uefaciens, Bacillus licheniformis, Bacillus pumilus Bacillus coagulans, Bacillus megaterium, and, Paenibacillus polymyxa.

Example 14

Preparation of a Wastewater Product from the Expanded Set of Microbes in Example 13

The dried microbial mix of Example 13 is diluted 1:100 with dextrose (Clintose® Industrial Dextrose). To this mix is added 3% by weight powdered soy lecithin (Nealanders International, Inc). The final microbial count is typically $1 \times 10^9$ CFU/g.

We claim:

1. A dry powder composition comprising a mixture of: a first bacterial component consisting of *Bacillus subtilis, Bacillus amyloliquefaciens, Bacillus licheniformis*, and *Bacillus pumilus*, wherein each *Bacillus* organism is individually aerobically fermented, harvested, freeze-dried, and ground to produce a powder having a mean particle size of about 200 microns, with greater than about 60% of the *Bacillus* particles in the size range between 100-800 microns; and a second bacterial component consisting of *Pediococcus acidilactici, Pediococcus pentosaceus* and *Lactobacillus plantarum*, wherein each *Pediococcus* and *Lactobacillus* organism is individually anaerobically fermented, harvested, freeze-dried, and ground to produce a powder having a mean particle size of about 200 microns, with greater than about 60% of the *Pediococcus* and *Lactobacillus* particles in the size range between 100-800 microns, wherein: the first bacterial component and the second bacterial component are the sole bacterial components; the composition upon addition to w ater fully disperses; and the ratio of the first bacterial component to the second bacterial component by weight is between 1:10 to 10:1.

2. The composition of claim 1, wherein the ratio of the first bacterial component to the second bacterial component by weight is 1:10.

3. The composition of claim 1, wherein the ratio of the *Pediococcus acidilactici, Pediococcus pentosaceus* and *Lactobacillus plantarum* of the second bacterial component is by weight 1:1:1.

4. The composition of claim 1, wherein the composition has a moisture content of less than about 5% by weight and a final bacterial concentration of between about $10^8$ to $10^{11}$ colony forming units (CFU) per gram of the composition.

5. The composition of claim 1, further comprising an inert carrier.

6. The composition of claim 5, wherein the inert carrier is dextrose monohydrate.

7. The composition of claim 6, wherein the dextrose monohydrate is at a concentration of about between 75-95% (w/w).

8. The composition of claim 1, further comprising an organic emulsifier.

9. The composition of claim 8, wherein the organic emulsifier is at a concentration of about between 2 to 5% (w/w).

10. The composition of claim 8, wherein in the organic emulsifier is soy lecithin.

11. A method of treating wastewater comprising contacting the wastewater with an effective amount of the composition of claim 1, w herein treating the wastewater includes decreasing biological oxygen demand (BOD), total suspended solids (TSS), total kjeldahl nitrogen (TKN), and fats, oils and grease (FOG) in the wastewater.

12. The method of claim 11, wherein the wastewater is municipal sewage, residential septic, or industrial wastewater.

13. The method of claim 12, wherein the industrial wastewater comprises food, fats, oils, grease, brewery, agriculture, or commodity waste.

14. A method of treating swimming pool water comprising contacting the water with an effective amount of the composition of claim 1, wherein treating the swimming pool water includes reducing scum in the swimming pool.

15. The method of claim 14, wherein the water is contacted by contacting a swimming pool filtration unit with the composition.

16. The method of claim 14, wherein the composition is embedded in a solid support.

17. A method of remediating wastewater from fruit or vegetable washing comprising contacting the wastewater with an effective amount of the composition of claim 1, wherein remediating the wastewater includes reducing latex concentration in the wastewater.

18. A method of treating the surface of a fruit or a vegetable, comprising contacting the fruit or the vegetable with an effective amount of the composition of claim 1, wherein the method removes organic material from the surface of the fruit or the vegetable.

19. The method of claim 18, wherein the fruit is banana.

20. A method of manufacturing the composition of claim 3, the method comprising the following steps:
a) individually aerobically fermenting each *Bacillus* organism;
b) individually anaerobically fermenting each *Pediococcus* and *Lactobacillus* organism;
c) harvesting each *Bacillus, Pediococcus* and *Lactobacillus* organism;
d) drying the harvested organisms;
e) grinding the dried organisms to produce a powder;
f) combining each of the *Bacillus* powders to produce a *Bacillus* mixture;
g) combining each of the *Pediococcus* and *Lactobacillus* powders in equal amounts to produce a *Pediococcus-Lactobacillus* mixture; and
h) combining the *Bacillus* mixture and the *Pediococcus-Lactobacillus* mixture at a ratio of between 1:10 to 10:1 by weight.

* * * * *